(12) United States Patent
Edelman et al.

(10) Patent No.: US 6,889,539 B2
(45) Date of Patent: May 10, 2005

(54) LOW DISTURBANCE PULSATILE FLOW SYSTEM

(75) Inventors: Elazer Edelman, Brookline, MA (US); Kumaran Kolandaivelu, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/629,471

(22) Filed: Jul. 29, 2003

(65) Prior Publication Data

US 2004/0206158 A1 Oct. 21, 2004

Related U.S. Application Data

(63) Continuation of application No. 09/804,936, filed on Mar. 13, 2001, now abandoned.
(60) Provisional application No. 60/188,723, filed on Mar. 13, 2000.

(51) Int. Cl.$^7$ ............................................... G01N 37/00
(52) U.S. Cl. ...................................... 73/64.41; 436/69
(58) Field of Search ...................... 73/37, 54.04, 54.05, 73/54.14, 54.23, 54.28, 64.41, 866.4; 436/69; 623/1.1

(56) References Cited

U.S. PATENT DOCUMENTS

| 5,271,898 A | 12/1993 | Wolf et al. |
| 5,913,896 A | 6/1999 | Boyle et al. |
| 6,043,871 A | * 3/2000 | Solen et al. ................... 356/39 |

OTHER PUBLICATIONS

Chandler, A.B., 1958, "In vitro thrombotic coagulation of the blood," Laboratory Investigation, 7, pp. 110–114.

Haycox, C.L., Ratner, B.D., 1993, "In vitro platelet interactions in whole human blood exposed to biomaterial surfaces: Insights on blood compatibility," 27, pp. 1181–1193.

Grabowski, E.F., 1988, "Effects of contrast media on erythrocyte and platelet interactions with endothelial cell monolayers exposed to flowing blood," Investigative Radiology, 23(Suppl 2) S351–358.

Goto, S., Handa, S., 1998, "Coronary thrombosis: Effects of blood flow in the mechanism of thrombus formation," Japanese Heart Journal, 39, pp. 579–596.

Beythian, C., Terres, W., Hamm, C.W., 1994, "In vitro model to test the thrombegenicity of coronary stents," Thrombosis Research, 75, pp. 581–590.

K. Gutensohn et al., 1997, "Flow cytometric analysis of coronary stent–induced alterations of platelet antigens in an in vitro model," Thrombosis Research, 86, pp. 49–56.

C. Beythian et al., 1999, "Influence of stent length and heparin coating on platelet activation: A flow cytometric analysis in a pulsed floating model," Thrombosis Research, 94, pp. 79–86.

A. Tamok et al., 1999, "Rapid in vitro biocompatibility assay of endovascular stents by flow cytometry using platelet activation and platelet–leukocyte aggregation," Cytometry (Communications in Clinical Cytometry), 38, pp. 30–39.

(Continued)

Primary Examiner—C D Garber
(74) Attorney, Agent, or Firm—Gauthier & Connors LLP

(57) ABSTRACT

A flow system device used for testing/creating fluid flow. The system comprises at least one fluid filled loop and a rotor stage for maintaining at least one rotor. The loop is positioned on the rotor. The device also includes a driving motor for rotating the rotor stage and a motion controller for controlling the speed and directional motion of the motor.

23 Claims, 8 Drawing Sheets

OTHER PUBLICATIONS

R.R. Makkar et al., 19998, "Effects of clopidogrel, aspirin and combined therapy in a porcine ex vivo model of high-shear induced stent thrombosis," European Heart Journal, 19, pp. 1538–1546.

S. Verheye et al., 2000, "Reduced thrombus formation by hyaluronic acid coating of endovascular devices," Arteriosclerosis Thrombosis, Vascular Biology, 20, pp. 1168–1172.

R.A. Schatz et al., 1991, "Clinical experience with the Palmaz–Schatz coronary stent: initial results of a multicenter study," Circulation, 83, pp. 148–161.

A. Shaknovich et al., 1994, "Subacute stent thrombosis in the STent REStenosis Study (STRESS): Clinical impact and predictive factors," Circulation, 90 (Suppl I), pp. I-650.

Brodkey, R.S., 1967, The Phenomena of Fluid Motions, pp. 129–134.

B. Savage et al., 1996, "Initiation of platelet adhesion by arrest onto fibrinogen or translocation on von Willebrand Factor," Cell, 84, pp. 289–297.

D. Basmadjian, 1989, "Embolization: Critical thrombus height, shear rates, and pulsatility. Patency of blood vessels," Journal of Biomedical Materials Research, 23, pp. 1315–1326.

D. Basmadjian, 1990, "The effect of flow and mass transport in thrombogenesis," Annals of Biomedical Engineering, 18, pp. 685–709.

G.S. Kassab et al., 1993, "Morphometry of pig coronary arterial trees," American Journal Physiology, 265 (Heart Circ. Physiol. 34), pp. H350–H365.

S. Baldwin, D. Basmadjian, 1994, "A mathematical model of thrombin production in blood coagulation, Part I: The sparsely covered membrane case," Annals of Biomedical Engineering, 22, pp. 357–370.

* cited by examiner

LOW DISTURBANCE PULSATILE FLOW SYSTEM

CROSS REFERENCED APPLICATION

This application is a continuation of U.S. patent application Ser. No. 09/804,936, filed on Mar. 13, 2001, which is now abandoned and incorporated herein by reference in its entirety, which claims priority from provisional application Ser. No. 60/188,723, filed on Mar. 13, 2000, also incorporated herein by reference in its entirety.

This invention was made with government support under Grant No. NIH-1-RO1-GM49030 awarded by the National Institutes of Health. The government has certain rights in the invention.

BACKGROUND OF THE INVENTION

The invention relates to the field of coronary implants, and in particular to a low disturbance, pulsatile, in vitro flow circuit for modeling coronary implant thrombosis.

Biocompatibility has been a major issue in the ability to use prosthetic implants in clinical settings. One such set of applications includes vascular prosthesis such as endoluminal stents or grafts to allow blood to flow either through or past a previously stenosed vascular segment. When such a foreign structure comes into contact with tissue and blood, a variety of biological consequences ensue. These reactions, ranging from thrombosis, to inflammation, to restenosis, can result in acute or long-term device failure. Not only is coagulation responsible for the obvious occurrences of acute thrombotic events, but sub-clinical levels have also been implicated as a player in the pathophysiology of restenosis through the release of chemical mediators and by providing a scaffold for the ingrowth of migrating and proliferating cells.

The thrombotic reaction is one of the earliest responses to implantation and by virtue of its potential for rapid acceleration and complete luminal occlusion, one of the most devastating. Forming clot not only serves as a scaffold for the ingrowth of migrating and proliferating cells, but as a source and reservoir for chemical mediators of these cellular events, such as platelet derived growth factor and thrombin. Elucidation and control of the thrombotic process is especially important for the continued use and development of vascular implants.

Vascular patency relies on a careful balance of chemical mediators and local fluid dynamics. With vascular injury, even as simple as the insertion of a small intravascular wire, profound micro-environmental changes ensue, altering blood flow and coaguability. A thrombus develops and propagates when the stimulatory forces cannot be balanced by the negative regulatory measures. Platelets adhere and activate at a given implantation site, potentiating the coagulation reactions by acting as an enzymatic surface and sequestering reactants both from flow and other inhibitory influences. These coagulation processes then potentiate further platelet activation directly via the production of mediators such as thrombin and indirectly by stabilizing the adherent platelets via a fibrin meshwork. Physiologically, these cellular and molecular systems interact in a highly inter-dependent manner to make thrombosis possible in the face of arterial flow conditions.

One difficulty that has limited the extensive examination of bioprosthetic thrombosis is the highly flow-dependent nature of thrombosis and lack of widely applicable flow models. Flow can affect the components of thrombosis either through physical shear dependent mechanism, such as von Willebrand's Factor dependent platelet activation, or through mass transport of cellular and molecular substances into and out of a given region. Thus, control and documentation of reproducible flows are essential to the study of the dynamically coupled cellular and protein pathways leading to implant thrombosis. Also, doing so in a controllable in vitro setting is desirable as individually and controllably perturbing the various thrombotic components is essential to studying the dynamically coupled cellular and protein pathways.

Various prior art flow systems have been developed in order to study the thrombotic process. One such method includes placing a loop partially filled with blood on a tilted turntable. As the table spins, gravity keeps the fluid at the bottom of the tube, creating flow. This method is known as the Chandler loop technique. It is not ideal as a large air/blood interface can cause protein aggregation and denaturation, creating a significant departure from the physiological situation. Furthermore, this method does not allow for arterial flow profiles to be obtained.

Another method for the investigation of flowing blood was the development of parallel-plate flow chambers. This apparatus is particularly useful in studying cellular interactions with a surface as the chambers are microscopically viewed in real time. However this is not helpful when studying actual coronary prosthetic configurations as the chambers and flow rates are not arterial in nature.

When studying coronary prosthesis, and in particular stents, one prior art method includes the use of a roller or peristaltic pump to drive flow through a length of tubing. The described setup utilizes a 3 mm ID, 82 cm long peristaltic tubing (PVC or silicon) filled with 6 ml of platelet rich plasma. A 3-way valve is used for the placement of fluid. The stent is expanded in a discontinuous connecting 4 mm ID segment. This methodology has recently been used to show variations in platelet activation, via Flow cytometry methodology and the clotting times for stents of different lengths and with heparin coatings, though it could not distinguish between tantilum and stainless steel stents. However, there are several factors that reduce the potential of this system to study stent thrombosis. One is the level of background noise that is created with the large surface area of peristaltic tubing and the roller pump's action. In order to keep the pump's background effects to a minimum, a low 8 ml/min flow rate was used, while actual mean flow rates of 50 ml/min are achieved in the coronary arteries with peak values normally reaching 100 ml/min. Furthermore, placing the stent in a discontinuous 4 mm region not only increases system background noise, but substantially perturbs the flow over the stent. Both the flow rate and stent placement create a dramatic misrepresentation of the dynamics of flow dependent thrombosis.

Another method that has recently been described as an in vitro evaluation of stent thrombosis includes a simple setup wherein blood is drained directly from a volunteer into a funnel connected to a length of tubing into which the stent is placed. The blood is directly collected into a tube and then analyzed for variations in platelet activation. This system reduces the background noise by using a shorter tubing length and no peristaltic pump. On the other hand, the signal is also reduced due to the one pass methodology rather than recirculation. Although some differences could be noted with certain stents, others were not significantly different than control runs, thus indicating the lack of sensitivity and that the flow rate was not controlled. Additionally, bleeding a volunteer requires a substantially greater amount of blood than recirculant setups.

Some animal in-vivo and ex-vivo models have been used. Although these have the ability to create physiological flows, they have a drawback in that there is a limit on the amount of control that is attainable in the system as parameter variation must be within life-sustaining margins. Therefore, studying the coupled nature of thrombus formation is difficult because the components cannot be varied to the extent that they may in an in-vitro setup. Many extraneous variables exist in in-vivo systems that could complicate the process being observed rendering unanalyzable results. Also interspecimen variation can create noise, which if large enough, could obscure potential findings. Another concern is that although observations may be made in one species, they may not be robust enough to occur in humans due to relative functional component differences. Practically, there are other issues, from the expense to the ethics, that must also be taken into account when using such systems. Though these issues limit what can be gained from in-vivo models, some studies have nonetheless been performed which are of relevance. For instance, Makkar et al., 1998, "Effects of lopidogrel, asprin, and combined therapy in a porcine ex-vivo model of high-shear induced stent thrombosis," *European Heart Journal.* 19(10), 1538–1546 show in an ex-vivo pig model that polishing or polyethylene oxide modified nitinol surfaces were less thrombogenic than nitinol surfaces.

Other types of studies have included clinical trials. These carry with them many of the same problems as the animal studies. Additionally, there is even less controllability as the welfare of the patient is the primary concern, with many observations being taken retrospectively. Although in the end, these trials must be performed to validate findings from other models, the preliminary use of models can be used to investigate processes in a more scientifically rigorous fashion, while decreasing patient risk in clinical trials. Therefore, it is desired to develop a more suitable in-vitro model of the coronary situation to aid in the study of vascular phenomenon such as thrombosis.

SUMMARY OF THE INVENTION

A model has been created to observe the physiological, controllable flows in a manner to create a large thrombotic signal, while minimizing the effects of background noise. This is accomplished by minimizing the length and discontinuities of a tubing loop into which a prosthetic, such as a stent or a graft, is placed. The loop is then filled with the desired blood constituents and spun about its axis in a prescribed fashion. This spinning is controlled in such a way as to modulate the inertial flow of the contained fluid through transmitted shear forces from the tubing wall, thereby creating a low disturbance flow.

An object of the present invention is to provide a low disturbance, pulsatile flow system used for testing/creating fluid flow.

Another object is to provide a system for testing the thrombotic effects of blood when a stent is positioned within the system.

A further object is to provide a method of using a low disturbance pulsatile flow system to study fluid flow.

An additional object is to provide a method to test for thrombotic effects.

Another object is to provide an improved connecting device such that two opposing ends of a tube are held in near perfect axial alignment, minimizing luminal discontinuity.

These and other objects, features and advantages of the present invention will become apparent in light of the following detailed description of preferred embodiments thereof, as illustrated in the accompanying drawings.

DETAILED DESCRIPTION OF THE INVENTION

Figure 1:
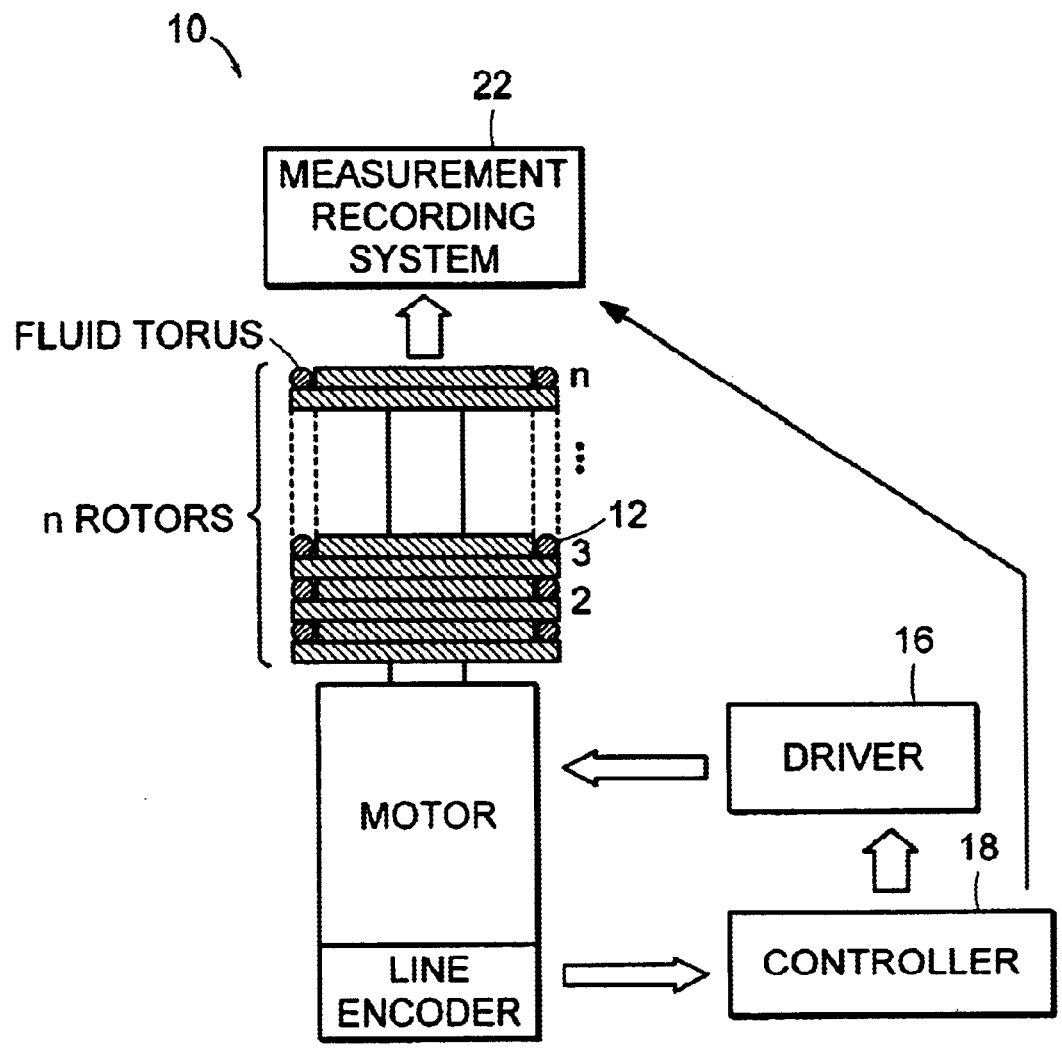
FIG. 1 is a diagrammatic illustration of a low-disturbance, pulsatile system device in accordance with the present invention.

As shown initially in FIG. 1, is a low-disturbance, pulsatile, in vitro flow device is generally shown at 10. The device includes a fluid torus 12, rotor-stage 14, driving motor 16, motion controller 16, and a measurement recording system 22 utilized to observe the physiological, controllable flows in a manner to create a large thrombotic signal. The system is usually utilized in an incubator, not shown, to keep the samples at a stable temperature. As described in detail below, this includes placing a stent 24 or a graft in a torus or loop 12, as seen in the Figures. The loop 12 is then filled with the desired blood constituents and spun about its axis in a prescribed fashion. This spinning is controlled in such a way as to modulate the inertial flow of the contained fluid through transmitted shear forces from the tubing wall, thereby creating a low disturbance flow.

Figure 2:
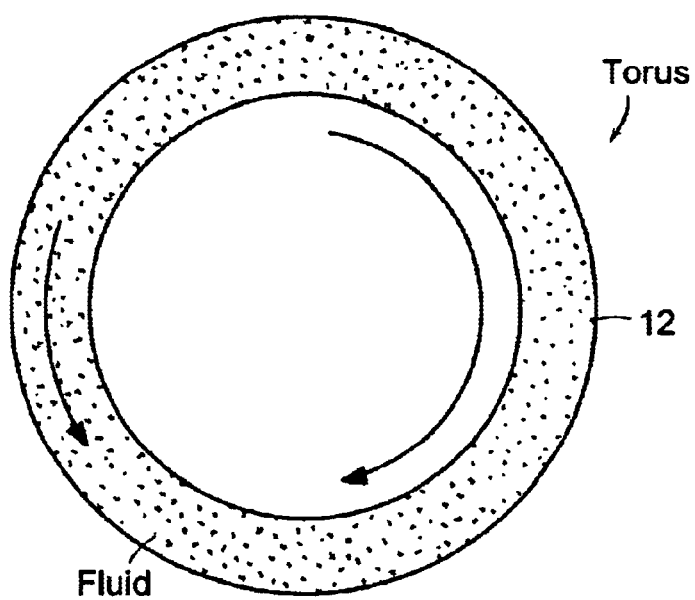
FIG. 2 is sectional view of a fluid fill torus.
Figure 3:
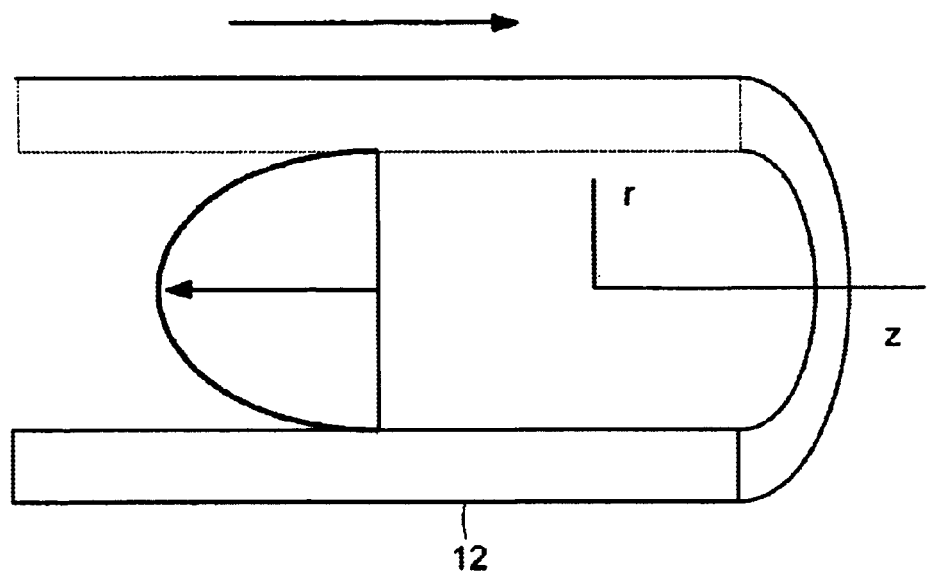
FIG. 3 is a sectional view of cylindrical pipe with linearly accelerating walls.

To create the desired flow profiles, the fluid-filled torus 12 is rotated about its axis. When impulsively started, there is inertial fluid motion relative to the toroid wall as shown in FIG. 2. As time passes, the fluid is accelerated due to momentum transfer into the fluid bulk via shear forces. If the driving torus is spinning at a constant angular velocity, the fluid eventually achieves solid body rotation coincident with the torus and relative motion ceases. However, should the loop maintain an acceleration, there continues to be relative motion, and hence, flow. The radial profile of this type of fluid motion is found by the Navier-Stokes equation. A critical simplifying assumption is that the fluid tube radius is much smaller than the torus radius, allowing streamline curvature affects to be neglected. Therefore, the system can be modeled as a straight, cylindrical pipe with linearly accelerating walls as seen in FIG. 3, and only the axial component of the Navier-Stokes equations need be considered.

In the case of flow in a circular pipe of constant cross sectional area, several terms can be eliminated, as there is an axial component of the velocity vector that changes with the radial dimension and with time. Assuming a reference frame that accelerates with the tube wall, the Navier-Stokes equations can be simplified to:

$$\left(\frac{\partial V_z}{\partial t}\right) = a + v\left(\frac{\partial^2 V_z}{\partial r^2} + \frac{1}{r}\left(\frac{\partial V_z}{\partial r}\right)\right) \quad (1)$$

where $V_z$ is the axial velocity, t is time, r is the radius, v is the kinematic viscosity, and a is the tube acceleration.

The steady state solution resembles that of pressure driven Pousille flow with the driving force given by the acceleration rather than an axial pressure gradient. Therefore, the method of flow creation not only drives flow in an undisturbed fashion, but also in a manner identical to the pressure driven case if the accelerations are scaled to appropriately match the would-be imposed pressure gradients (divided by the density).

A solution to this partial differential equation with the customary pipe boundary conditions ($V_z=0$ at $r=R$, $dV_z/dr=0$ at $r=0$) and an initial condition of $V_z=0$ with a constant acceleration, a, is given by:

$$V_z = \frac{c^2 a}{4v}\left[1 - \frac{r^2}{c^2} - 8\sum_{n=1}^{\infty}\frac{J_0(\gamma_n r/c)}{\gamma_n^3 J_1(\gamma_n)}e^{-\gamma_n^2 vt/c^2}\right] \quad (2)$$

The time dependence of this equation is governed by a time constant dependent on the inverse of the kinematic viscosity, v, and the tube radius, c, squared. Furthermore, as t approaches infinity, the solution approaches the Pousille-like steady state solution.

Equation 2 illustrates that by controlling the wall accelerations, the flow within the tube can be modulated with the steady state flow rates being linearly related to the tube accelerations. However, since the system time constant (0.1 sec) is of a similar order of magnitude as the heart rate (~1 sec), it must be noted that the actual developed flow rates may not be the steady (or quasi-steady) state values for a given acceleration profile. For a true flow pattern, a numerical simulation with the imposed acceleration profile can be obtained. Still, the analytical results give sufficient insight into the suitability of the methodology, as well as several factors such as accelerations, time constants, and parameter dependence which must be considered when designing a modeling system.

Although a relative flow can be created through some pattern of wall accelerations, one issue is that keeping a constant flow requires a constant acceleration. Moreover, a net positive flow requires a net positive acceleration resulting in infinite (or at least impractically large) angular velocities. Since the coronary arteries run through the myocardial tissue of the heart, the intramural pressure rises during contraction (systole), blocking off flow in the coronary arteries. Conversely, during relaxation (diastole), the wall pressure is reduced and flow is driven via the higher arterial pressure. Thus, unlike other flows in the body, most coronary flow takes place during diastole.

Figure 10:
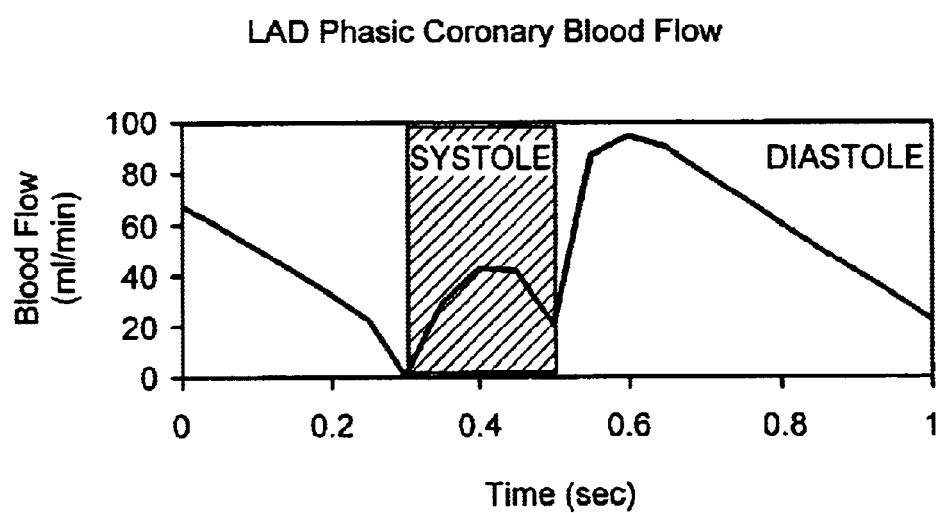
FIG. 10 is a graph of a coronary blood phase.

As seen in FIG. 10, the left anterior descending coronary flow actually comes to a halt. This sets up a situation where the acceleration of the loop can be reduced to zero allowing solid body rotation. However, at this point, the absolute velocity of the loop in the inertial reference frame will be greater than before the cycle had begun having just gone through a period of accelerations to achieve the desired flow profile. To begin another cycle in the same direction would mean again adding to the net uni-directional loop velocity, quickly reaching the maximal velocity limits of the motor. Instead, two alternative options exist: 1) introducing a one-way valve or 2) accepting bi-directional flow.

In a one-way valve system, when the fluid within the torus has reached a state of zero flow, the loop can be rapidly stopped from its constant angular velocity. This creates a negative impulsive wall velocity that creates flow in the opposite direction. However, by virtue of the directional valve, the fluid can be kept in solid body rotation and brought to rest in the inertial reference frame along with the torus. From this point, the acceleration pattern required for a desired flow profile can begin again and cycle indefinitely without a compounding net angular velocity.

Although this technique could be employed for certain applications, it is undesirable for the purposes of studying thrombosis. Such a valve would increase the thrombotic background potential of the system, both from its physical presence, and the imposed water-hammer effect when the fluid is jerked to a halt.

The second possibility is to allow bi-directional flow by following each loop acceleration profile with a symmetric deceleration, thereby bounding the angular velocity. The reversal of flow creates some concerns at macroscopic, microscopic, and molecular levels. Alternating flow direction means an alternating embolic shear force. This acts from the level of initial platelet adherence to that of macroscopic thrombi. Platelet adherence to a surface is generally characterized by a rolling and sticking phase. Since the duration of this process, during which an oscillating shear force might be imagined to cause a difference, is much less than that of a heart beat (system oscillatory period), the reversing shear is assumed to have a small effect. However, as the thrombus and imposed embolizing force grow, the oscillating shear may invoke a fatigue type failure response in the fibrillar connections, thereby increasing the probability of detachment. This is an important in-vivo occurrence, however it is of little consequence in the in vitro model since by the time macroscopic emboli form, much of the highly amplified thrombotic phenomenon under study would have already been determined. The changes in embolizing probability would simply affect the final stage of luminal blockage.

Oscillating flow affects mass transport. One factor is the change in convective flow patterns created by uni vs bi-directional flow. This is more of an issue at higher Reynolds's numbers, however, the small values i.e. <10 considered means that the flow and shear around obstacles (such as stent struts) is essentially symmetric. Therefore, regardless of flow direction, instantaneous species flux phenomenon should be governed by similar processes in the vicinity of wall protrusions as these are dependent on a shear dependent mass transport coefficient and an independent reaction rate coefficient.

Figure 4A:
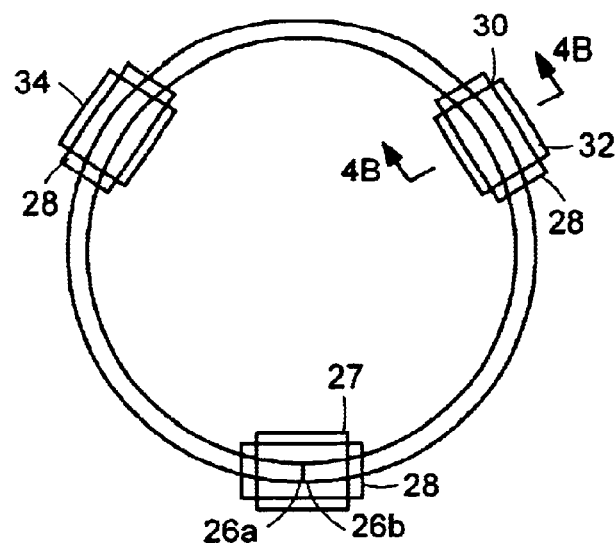
FIG. 4A is a sectional view of a loop including the connectors.
Figure 4B:
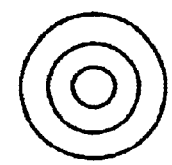
FIG. 4B is a sectional view of FIG. 4A taken along line 4B.

A schematic of the fluid torus 12 is show in FIGS. 4A and 4B. In the current embodiment, the toroids are made of a 24 cm circumferential loop of ⅛" ID::5/32" OD S-50-HL Tygon tubing. The connecting ends 26a, 26b of the loop have been squarely cut with the axial dimension to ensure a matching end-to-end fit. This connection is held via a 1.75 cm overlapping segment 28 of S-50-HL Tygon tubing of 3/16" ID::5/16" OD. The close OD/ID match provides a good compression fit and axial alignment. Further support is provided by a 1 cm elastic band 30 made from a silicon tube (Silastic) of ¼" ID::⅜" OD placed over the joiner segment of tygon. The elastic radial compression provided by the segment's smaller ID assures a suitable joint connection.

The connectors 27 allow the tubing circuit to be free of geometry and luminal surface discontinuities. The application of the internal pressures tends to strengthen the joint, rather than weaken it. The connector is such that the tube has an inner diameter equal to the outer diameter of the circuit's tube diameter, and an elastic outer sleeve that slightly compresses the formed joint to provide a tightly sealed connection.

Two similar structures 32, 34 are slid onto the ⅛" loop at equally spaced 120 degree intervals in order to cause the least deviation in toroid curvature possible as the structures provide some rigidity to the underlying fluid loop segment. The two additional sleeves 32, 34 serve as outlet and inlet ports for the replacement of the loop's contained air by the desired fluid (ie. blood/plasma/buffer). This is accomplished by sliding a needle under the outer most elastic sleeve, and then, pushing the needle through the middle sleeve and inner loop layers at approximately a 45 degree angle. Small-bore needles are used to create the smallest possible disturbance to the loop's inner, fluid-contact surface. The elastic outer sleeve 30 provides a final seal to the escape of loop contents. A 26-gauge needle is used at one of the ports which serves as an outlet for the evacuation of air. A larger bore is used for the injection of cellular fluid to limit the handling trauma. Generally, a 19-gauge phlebotomy needle is used for the transfer of blood products as a compromise between the need for a small injection port and an untraumatic injection.

An estimate of the diameter of a normal adult left anterior descending coronary branch is 3–3.5 mm. The ⅛" ID tube falls within this range at 3.175 mm. The OD of ⁵⁄₃₂". It is important to have as little extraneous surface contact as possible to reduce the circuit's background thrombotic potential. The small, contained recirculating volume allows the thrombotic process to proceed in an amplified fashion. The tube 12 also has to be long enough so that the assumptions of linear flow would remain a valid approximation. As a 3" diameter is nearly 2.5 orders of magnitude larger than the ⅛" ID of the loop and the loop length 12 is 24 cm. However, depending on the relative need to reduce surface area/recirculating volume while keeping secondary, curvature related flow effects to a minimum, the length can be modified to other values.

The Tygon tubing has low protein absorption and bioreactivity. Though this tubing was chosen for its low-reactivity, the inertial mechanism which drives the flow is not limited to any type of tubing (compliant tubing is used in peristaltic pumps). If desired, the tubing is replaceable with one of a given surface quality whose properties are to be study. Furthermore, the tubing can be completely lined or coated with a substance. This is of particular value when investigating processes such as thrombosis, where the endothelium and underlying composition plays an important role. The tubing can be coated with a type-I collagen surface as a rough approximation of the subendothelium. Confluent endothelialization is also possible since there is no disturbance (structural or dynamic) of the inner loop surface once the torus 12 is formed.

Figure 5B:
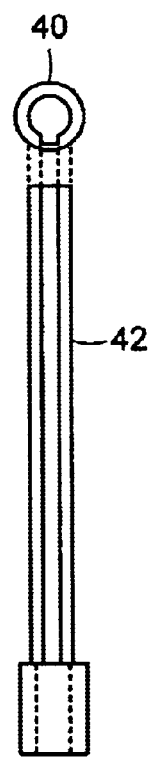
FIG. 5B is a sectional view of the shaft and cap.
Figure 5A:
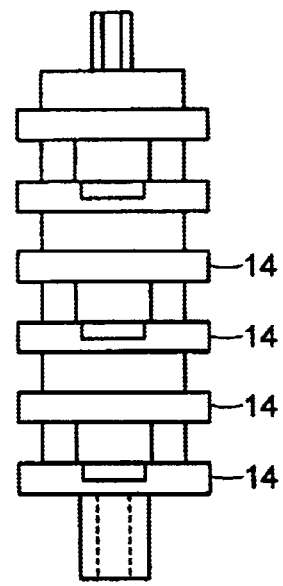
FIG. 5A is a sectional view of the rotors mounted on a shaft.

The loop 12 is then fit onto a rotor platform or stage 14 and placed in axial alignment with other loops to be tested under the same flow conditions as seen in FIGS. 5A and 5B. Although any number of loops 12 may be selected, the embodied system accommodates six simultaneous runs via six modular rotor platforms 14. The entire rotor system is then driven through a desired angular motion profile via the motor 16 and controller system 18. This motion creates the bidirectional flows which are measured via onboard flow transducers built into the rotor stages. Each transducer sends the flow from a particular fluid loop to the measuring/recording system, which can be used to instantaneously monitor the flow profiles and fluidity of the blood.

Figure 6:
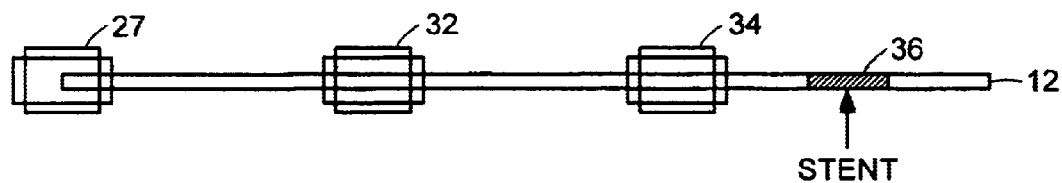
FIG. 6 is a sectional view of the loop before being connected including a stent.

The prototypical implants include 7–9 NIR stents 36, as seen in FIG. 6, and have a diameter of 3.5 mm and are 9 mm in length. They are obtained from Medinol Ltd. (Jerusalem, ISRAEL). Stainless steel and gold coated surfaces were selected to offer a variable thrombotic potential. The stents 36 were expanded 1 cm from the end of a given sample tube (9.5" long ⅛" ID ⁵⁄₃₂" od 3350 Tygon tubing). The ID dimension was between 3–3.5 mm and an OD that was imposed by the wall thickness requirements of the flow transducers. The length was determined by a balance between minimizing the extraneous surface area while keeping the loop curvature considerably larger than the tube diameter.

Figure 7A:
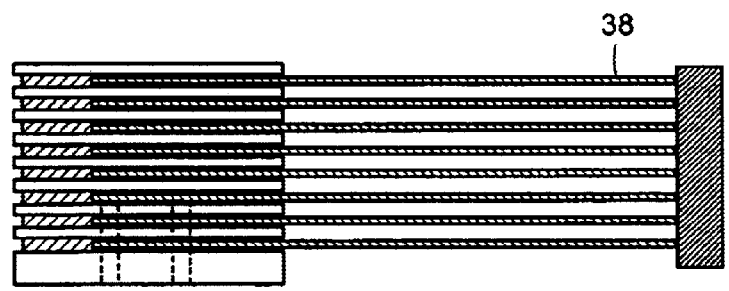
FIG. 7 is a sectional view of the couplings of the measuring system.
Figure 7B:
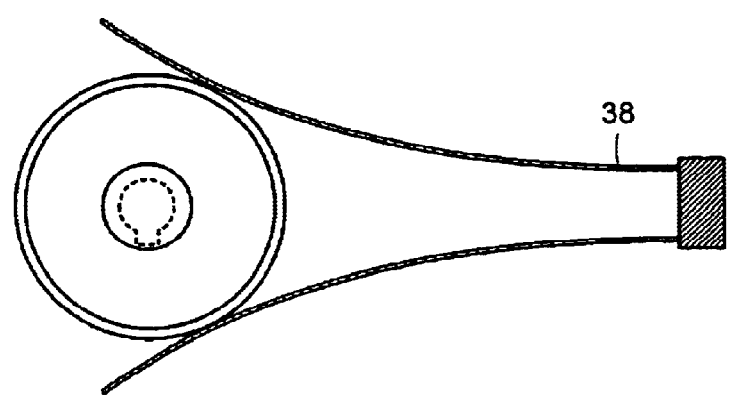

After the tubes were closed into their loop format they were filled with the desired blood components. The loops were fit onto a rotor platform 14 and placed in axial alignment with the other loops to be tested under the same flow conditions. The entire rotor system is driven through a desired angular motion profile via the motor/controller system 18, and held at a constant 37° C. in the incubator. The motion created pulsatile type flows which are measured via onboard Transonic flow transducers built into the rotor stages. Each transducer sent the flow from a particular fluid loop, through the rotary electric coupling 38 of FIG. 7 to the recording system, (LAB-PC/LABTECH software v8.2 manufactured by Laboratory Technologies Corporation), which was used to instantaneously monitor the flow profiles and fluidity of the blood in a given loop.

The rotors are the discoid platforms upon which the fluid loops are held. In the system that was built, there are six such rotors, accommodating six loops. FIG. 5A shows the design of an individual rotor (×3 orientation A/×3 orientation B). Each was manufactured out of a stock of 3" diameter delrin plastic. The rotors include a grooved, resting stage for the fluid loop, a keyed axial hole for rotor stacking and alignment of the rotors, a chiral notch for the placement of the flow transducer, and a shaft or slot 44 through which the transducer connections may be passed. The notch chirality allows sequential rotors to be stacked with the probes facing opposite directions in order to minimize asymmetrical loading. With the current rotor system's shaft, six rotor stages can be stacked on a shaft 42, along with a cap structure that serves as a location for on-board instrumentation. A centered hole allows for axial coupling to the motor.

The rotors were placed at a 180 degree shift for the A and B orientations. This chirality allows the sequential rotors to be placed one on top of the other, with the probes facing opposite directions. In doing so, the forces produced on the motor axis do to asymmetry are minimized.

Figure 8:
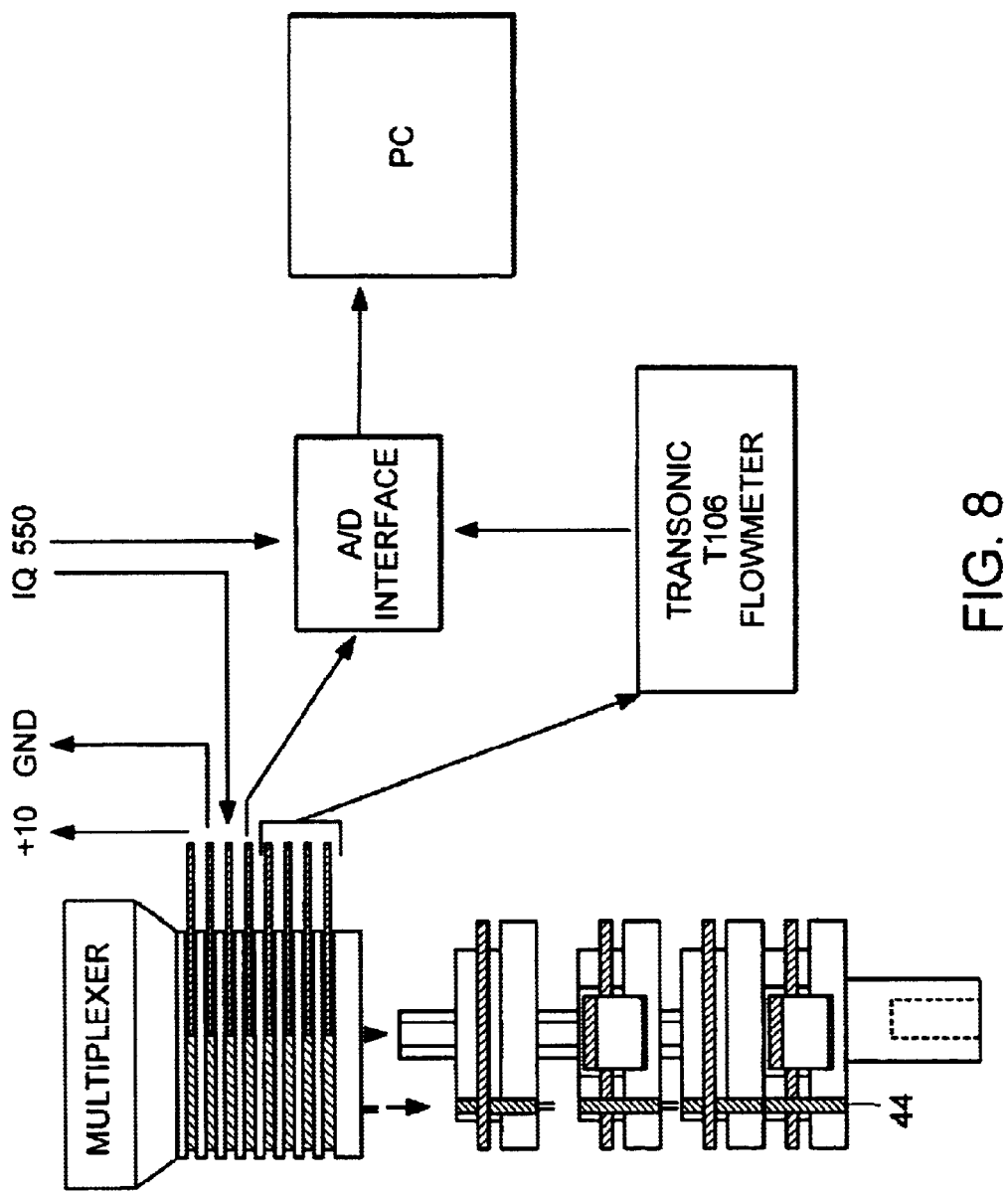
FIG. 8 is a schematic view of the system including the measuring system.

The rotor system's shaft is shown in FIG. 8 along with a diagram depicting six stacked, alternating rotor stages. The shaft was machined from a 1" diameter stock of delrin and is in two sections. The top section has been reduced to a diameter of 1.59 cm to accommodate the stackable rotors. The entire rotor system was driven through a desired angular motion profile via the motor/controller system, and held at a constant 37° C. in the incubator. The bottom section remained at the initial stock diameter of 1". A centered 0.5" diameter hole was drilled into it to allow for an axial coupling to the motor.

The shaft 42 extends past the length of six combined rotor heights. This allows for the placement of a cap structure 40 that could serve as a location for on-board instrumentation for the transducers.

The torque, T, needed to drive the system is simply the peak acceleration times the moment of inertia of the rotor/motor setup, assuming negligible friction effects. The peak torque is determined from the maximum angular acceleration required to drive the fluid, which in turn, is given by the maximum flow rates required. Peak physiological flow rates are around 100 ml/min in the coronary arteries (averaging ~33 ml/min). To achieve this flow at steady-state, equation 2 yields a wall acceleration of 2.67 m/sec^2, or an angular acceleration of 70 rad/sec^2 for a 3" diameter loop. To allow for a broader range of possibilities, the maximal acceleration was taken to be 175 rad/sec^2. The moment of inertia is estimated assuming the rotor was a solid delrin cylinder 3" in diameter and 27" in length with a corresponding mass of 1.2 kg to allow for an overestimate of the moment. The values result in a moment of inertia of 8.5e-4 Nms^2, and a corresponding peak torque of 0.15 N/m (670 oz/in).

In order to determine the maximal operating speed, an estimate of the speed required to accommodate one pulse is determined. A high estimate is found by taking the required acceleration for peak steady state flow (70 rad/sec^2) and multiplying this by the duration of one pulse. The pulse, which represents a heart beat, is approximately 1 sec (60 beats/min). To allot for changes in rate for a wider range of possible experiments, a 2 sec duration was used (30 beats/min). This yields a maximum angular velocity of 140 rad/sec (1340 rpm).

The driving motor is an Electrocraft NEMA 42C DC servo-brush motor. The NEMA 42C model provides a peak torque of 720 oz-in and a maximum, absolute operating speed of 4800 rpm, allowing for 6 uni-directional beats if desired.

The components of the motor control system integrate readily and allow for the generation of specific flow profiles. These components include a Renco RM15 Encoder, an Electro-Craft IQ-550 Position Control Module, an Electro-Craft Max-100 PWM Servo Drive, and a Windows compatible PC terminal running IQ Master software. The motor used to drive the system was an Electrocraft NEMA 42C DC servo-brush motor.

The components are interchangeable and are easily adjusted via the programmable controller through software rather than hardware means. Therefore, various flow profiles can be readily made and modified according to the desired experiment.

To measure the loop flow rates, Transonic 3CA flow probe leads are connected to a specially constructed junction on each rotor stage as illustrated in FIG. 8. Upon stacking, the male connector junctions on a given rotor stage allow communication with the female junctions on the stage immediately below it. Thus, each stacked rotor is hardwired to all of the probes. This design allows the stages to be modular for loading and possible future expansion, with the top most stage relaying all probe signals to the on-board probe multiplexer. The signals were passed sequentially to a Transonic T106 Flowmeter which outputs a voltage signal, recordable on a computer via a National Instruments LAB-PC A/D interface and LABTECH Version 8.1 software package. The trigger to sequentially switch probes is provided by the high to low or low to high state change of a digital output pin on the IQ 550 controller. This switch was programmed to occur after each flow cycle or beat. In this method, all of the probes' signals were merged into a continuous waveform. A final signal is sent from the multiplexer to the computer encoding a specific probe label. Therefore, with the waveform and corresponding probe label information, an individual fluid loop can be monitored throughout the time course of an experiment.

An eight lead rotary electrical coupling interfaces the rotating loop reference frame with the inertial frame. The onboard multiplexer probe output is wired to four of the rotary couplings as seen in FIG. 8. Two additional couplings provide power (+10V,GND) to the multiplexer. The last two lines provide contacts for the probe switch trigger and the probe label. Although the system can monitor and record the full flow profiles in the fluid loops, only the peak flow values were stored to disk in actual thrombosis experiments to reduce the amount of data storage. These peaks effectively convey information on change in the fluidity of the blood and luminal potency.

On each rotor stage, the four probe leads are passed to the connector shaft and soldered onto a given pin on a specially constructed 24 lead connector. Once the proper connections are made, the pieces are press fit into the connector shaft on the corresponding rotor stage. Upon stacking, the male junctions on a given rotor stage allowed 24 pin communication with the female junctions on the stage immediately below it. In such a manner, each stacked rotor stage was essentially hardwired to all of the probes (up to 6 in the current embodiment) via the 24 pin connections. This design allowed the stages to be modular for loading and possible future expansion purposes, with the top most stage relaying all probe signals to the probe multiplexer.

The multiplexer (powered by a TENMA 30V/3A adjustable power supply set at 10 V) is used to relay the probe signals in a sequential order to the flow meter which is only equipped to handle a single probe. To do this, a BASIC Stamp II Microcontroller (Parallax, Inc.) is used as a switcher to send a binary signal to a given lead (1–6) corresponding to the desired probe. This signal is then sent through a power amplifying stage to provide the current needed to trigger a single pole/quadruple throw telecommunications relay. The four poles of the relay are normally open. Upon activation, a connection is closed between the four leads of the selected probe and four common, non-specific output leads.

The output of the multiplexer is then sent to the T106 Flow meter, which is used to power the transducers and convert the probe output into a voltage signal representing the bulk flow (1V=50 ml/min). This is directly recorded on the LABVIEW software via the A/D interface. However, each of the probes' signals is merged into a continuous waveform. To know which probe was being recorded from at a particular time, a final signal was sent from the multiplexer to the PC encoding a probe label. Therefore, with the waveform and corresponding probe label information, an individual fluid loop could be monitored throughout the course of an experiment.

Although the system could monitor and record the full flow profiles in the fluid loops, only the peak flow values were stored to disk in actual thrombosis experiments to reduce the amount of data. These peaks would effectively convey information on change in the fluidity of the blood. The compression was performed in real-time using the LABVIEW software capabilities. To do this the IQ550 was programmed to send a brief 5V pulse to the PC during the peak acceleration signaling a consistent time point in each flow profile to be sampled, corresponding to the peak flow. To ensure a good sample value, 5 samples were taken at a rate of 50 Hz and averaged into a single peak value.

Figure 11:
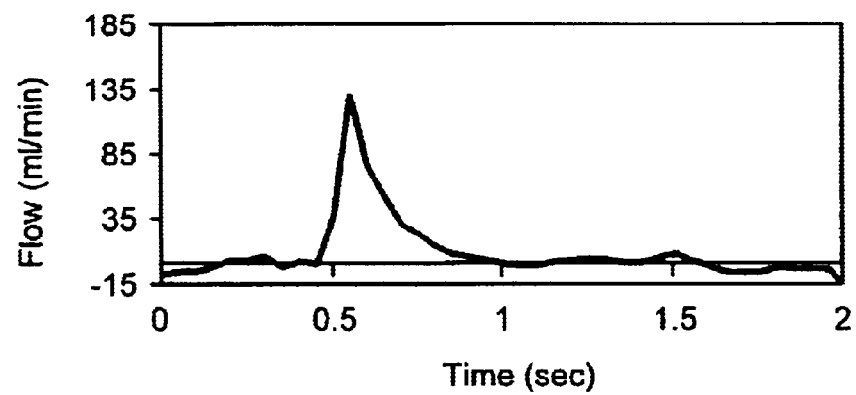
FIG. 11 is a graph of an impulse profile.

To test the mechanical capabilities of the system, first an impulse profile was generated, as seen in FIG. 11. This profile reveals that the up phase indicates the maximal rate of flow onset. With a true velocity step, this onset is also instantaneous. However, due to the realistic limitations of rotor inertia, friction, and peak torque, there is a deviation from the ideal impulse. The example above shows this deviation, where it takes 0.1 sec to achieve the peak flow. Another aspect that can be observed is the maximal rate of flow decay. Theoretically, a time constant of 0.1 seconds was determined, meaning that after 4 intervals, the flow would essentially drop to 0 (98% of original value). In reality, a similar time constant of 0.1 seconds is obtained, with the flow dropping to a 98% level in approximately 0.4 sec.

Figure 12A:
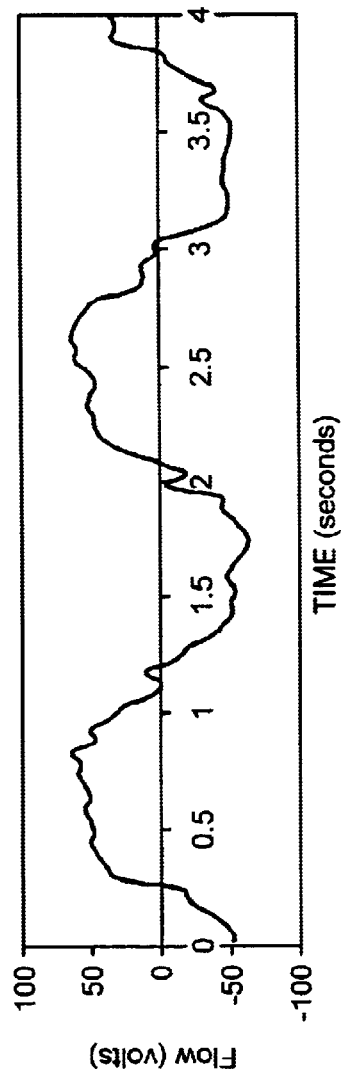
FIGS. 12A, B & C are graphs illustrating square, triangular and sine waves.
Figure 12B:
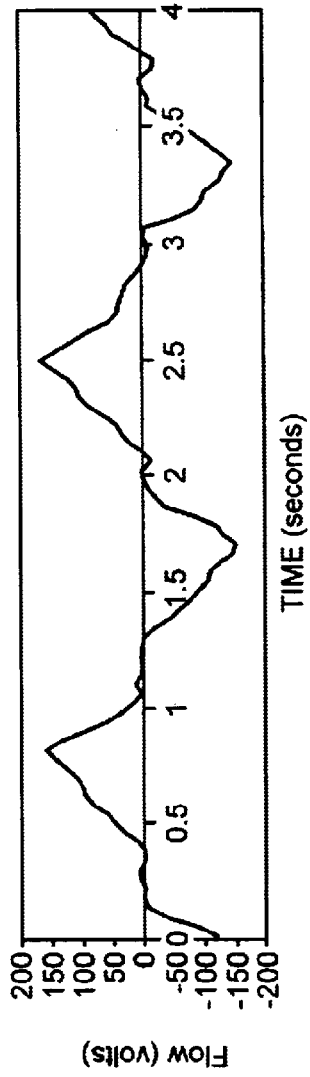
Figure 12C:
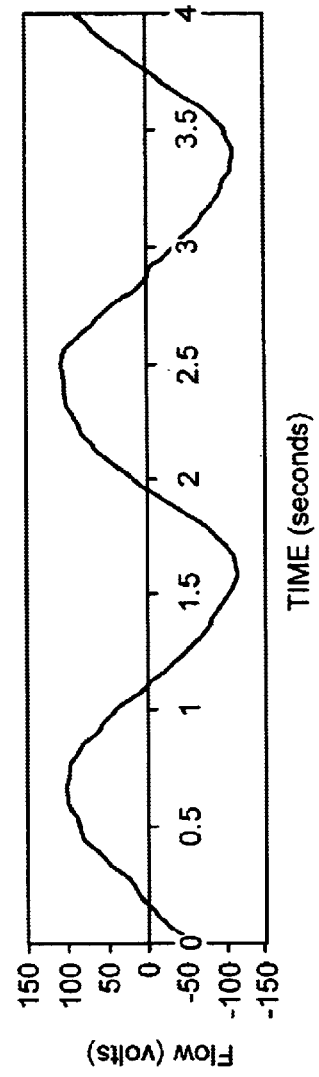

The impulse is an important function in that any other function can be broken down into a summed set of weighted impulses (Green's Functions). Thus, the realistic impulse-like function gives the limiting building block from which other functions can be composed. Some examples are square, triangular, sine waves, as seen in FIG. 12 and still other flows are possible.

Each pattern has a frequency of 1.11 Hz. However, the amplitudes vary from 50 ml/min for the square wave, to 100 ml/min for the sine wave, to 160 ml/min for the triangular wave. This variation is the result of the rotor acceleration profiles, which are bounded at equal peak angular velocities for each case. Therefore, since the square wave had its peak acceleration through out most of its cycle, this acceleration had to be smaller in magnitude than that of the sine or triangular wave (where the acceleration was varying through out the cycle) in order to keep similar limits on the loop angular velocity.

The flow is periodic and bi-directional in nature. This type of oscillation is necessary in the methodology used to create flow, as it was deemed more important to eliminate the high thrombotic background levels that would have been created through the use of a uni-directional valve setup.

The pliability of the system allows wave characteristics such as frequency and amplitude to be readily varied according to the experimental protocol. Furthermore the system allows for variation of more detailed parameters such as the systolic:diastolic ratio if desired.

The system is utilized to study prosthetic thrombosis. In order to do this, a source of blood and prototypical implants are required. Blood was obtained from the American Red Cross. The quantities of blood available made it possible to run several experiments on the same batch of blood, further limiting external variability. Secondly, the blood was obtained in pre-separated components. This allowed a mixing of components in any desired ratio (to assess, for example, the influence of a small recirculant volume on the experimental findings). For the following experiments, fresh frozen plasma and fresh platelets concentrates (both anticoagulated with 10 mmol citrate) were utilized as these contained the key ingredients of classical thrombosis, neglecting the red and white blood cells in the first level of study.

Type AB+ fresh frozen plasma (FFP) with a prescribed storage life of 6 months post-collection was stored at −20° C. The plasma was thawed in a 37° C. water bath for 45 minutes and then spun down at 10000 G's to eliminate any debris (particularly cellular matter such as preformed platelet microvesicles). The supernatant (upper 80%) was then filtered 4 times threw a 0.2 um filter to further ensure clean FFP. The platelets (type AB+PRP) were obtained within one day of collection and stored on a 70 RPM rocker at 22° C. These were used within the first two days post-collection as was justified from the robustness of findings when compared with freshly drawn volunteer platelets.

One hour before a planned experiment, the platelets were added to the FFP in the desired ratio and returned to the rocker. This equilibration in fresh plasma has been shown to revive the platelets from some of the shock they experience during the storage process. For all of the following preliminary experiments, a constant ratio of 1:4 PRP to FFP was used. Each loop required 2.5 ml (0.6 ml allotted for leeway) of the FFP/platelet mix. To reduce experimental error from mixing and handling variation, the total volume of the suspension for a given run is pooled and prepared in a single tube.

The prototypical implant chosen was a polished 7–9 stainless steel NIR stent obtained from Medinol. While the platelets were equilibrating in the filtered FFP, the stents were expanded in the ⅛" ID tygon tubing via a 36 mm Maxxum 3.5 SCIMED balloon catheter to a pressure of 12 atm. For consistency, they were all placed 1 cm from one end as shown in FIG. 6. Since the tube was symmetric, either end was acceptable with the middle third being avoided, as this was the site of flow measurement.

Once all of the stents were placed in the tubes, the tubes were closed into their loop format ensuring a gapless fit. When the plasma/platelet mix was ready, 5M Ca2+ was added to bring the sample to an additional 10 mmol Ca2+ concentration, negating the citrate's anticoagulant chelating effect. The fluid loops were then filled with the plasma/platelet mix as previously described via the 19-gauge needle and placed onto the rotors. This process was sequentially performed as rapidly as possible while ensuring safe handling of the blood components and proper filling of the tubes (i.e. no air bubbles). Once complete, the rotors were placed onto the rotor shaft and spun according to the desired motion profile. For the maximum six loops, the filling procedure took approximately five minutes from start to spin. The time could be further reduced, either through multiple participation or a novel filling method.

Figure 9:
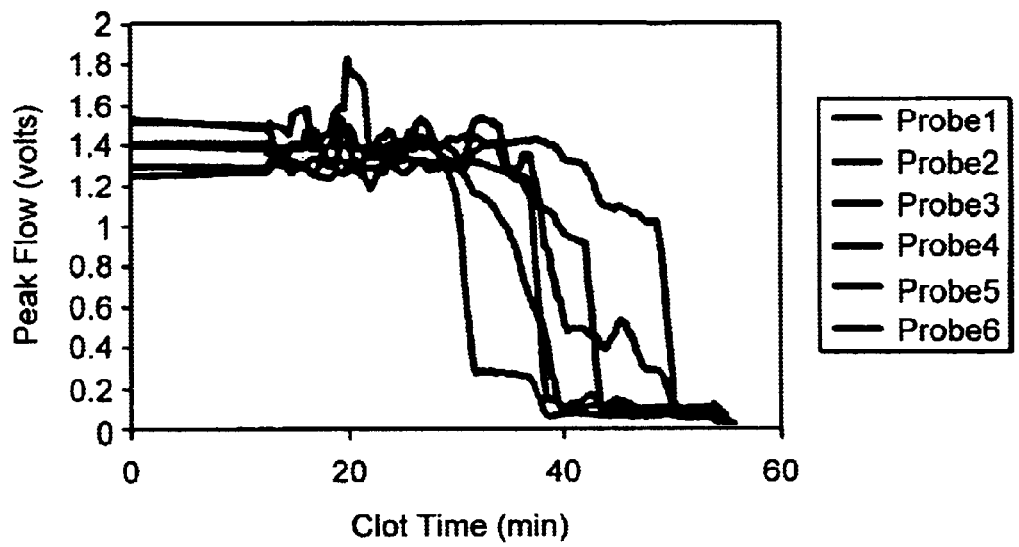
FIG. 9 is a graph of a sample test.

As an initial test, six stents were positioned in their respective fluid loops and run through the described protocol. The results obtained after parsing the data according to the probe label and running a 5-point moving average are shown in FIG. 9.

In this figure, each line represents an individual fluid loop. The two predominant characteristics of these lines are an initial constant flow rate followed by a fairly rapid drop off to zero flow.

The initial flows in each loop are identical since they all have the same dimensions, fluid properties, and driving motion profiles. However, a discrepancy can be seen in the graph as there is some spread in the start-up flow rates. This variation is due to the fact that the meter is hard calibrated for a specific flow probes (#1's) signal while the multiplexer passes six different signals to it. To correct this, each signal can be re-calibrated according to these initial deviations where identical fluid conditions are known to exist.

The drop off point indicates when the thrombus has blocked of the flow. If a zero flow condition is taken as the end point, an average clotting time of 43.1 min with a standard deviation of 6.8 min is obtained for the given run. From it, we can say that with a sample size of 10, two comparative stents of equal pool variance would have to have an average clotting time difference of at least 5.3 min in order to have a 95% confidence in their differential response (two-tailed p-value <0.05). By decreasing the standard deviation, the system gains power by being able to statistically distinguish smaller inter-stent differences in a given sample size.

Figure 13:
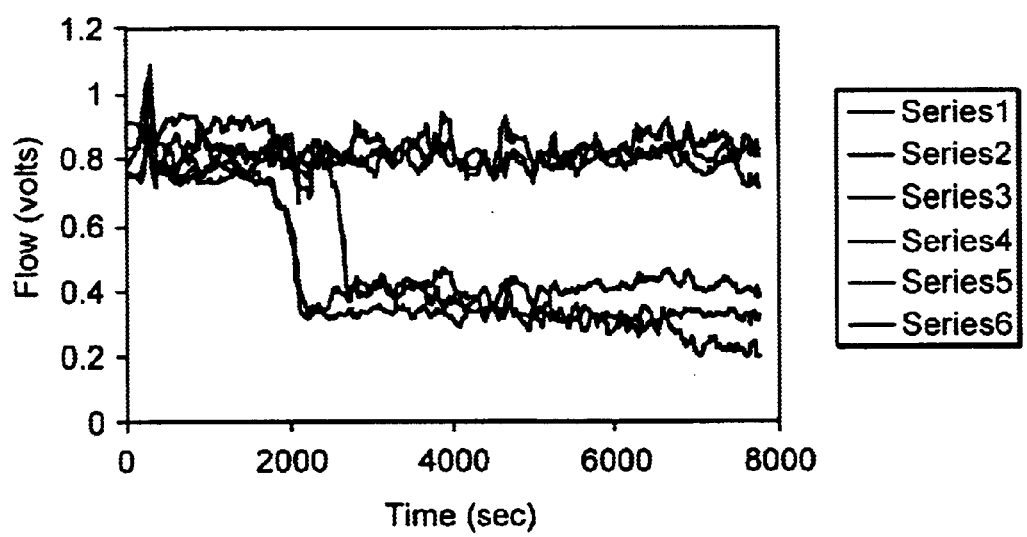
FIG. 13 is a graph illustrating background noise.

Another test of the system's validity and circuit noise levels is to compare a trial of three stents to three empty control tubes, as seen in FIG. 13. The initial flow period followed by a drop off is witnessed in the stented samples, with an average clotting time of 39.1+/−1.7 min. The stentless controls, however, remain unthrombosed for the 2.5 hour duration of the test indicating the sufficiently low levels of extraneous thombotic potential. The variation is stented loop clotting times between this run and the previous example (39.1 min vs 43.1 min) could be due to variations is blood component batches.

The proposed design is an in-vitro method that minimizes the background noise in a flow circuit to allow controllable, sensitive studies to be performed in a pliable coronary vascular setting. Furthermore, theoretical analysis revealed that these flows are identical in nature to that of pressure-driven flows. As a biological test of the system's capabilities, the thrombotic potential of a stent was assessed by performing trials on stented loops. In these trials, the peak flow data show an essentially binary phenomenon, characterized by an initial flow rate which quickly dropped off to zero as the thrombus occluded the circuit. Stentless control loops remained unoccluded for the duration of the trials, indicating the sufficiently low levels of background thrombosis.

While the current application of the described flow system is in studying coronary thrombosis, its use can be generalized to other situations where a carefully controlled pulsatile flow is required with adjustments (loop characteristics, uni/bi directional flow issue, etc) being made to suit the different requirements.

Although the present invention has been shown and described with respect to several preferred embodiments thereof, various changes, omissions and additions to the form and detail thereof, may be made therein, without departing from the spirit and scope of the invention.

What is claimed is:

1. A flow system device used for creating, monitoring, and controlling specific modifiable fluid flow patterns, said system comprising:
   at least one fluid filled loop;
   a rotor stage for maintaining at least one rotor, said loop positioned on said rotor;
   a driving motor for rotating said rotor stage;
   a motion controller for controlling the speed and directional motion of said motor;
   an external measurement system to observe, record, and control the contained loop flow within said at least one loop.

2. The flow system device of claim 1 wherein a vascular prosthesis is placed within the tube.

3. The flow system device of claim 2, wherein said vascular prosthesis is a stent or graft.

4. The flow system device of claim 2 wherein the stents are coated with gold or stainless steel.

5. The flow system device of claim 1 wherein the created fluid flow is bidirectional.

6. The flow system device of claim 5 wherein the specific fluid flow pattern produced and observed is that of coronary flow.

7. The flow system device of claim 1 wherein the loop includes a one way valve.

8. The flow system device of claim 1 wherein the system included six rotors with six corresponding fluid filled loops.

9. The flow system device of claim 1 wherein the fluid is blood.

10. The flow system of claim 1 wherein a biological signal is created.

11. The flow system device of claim 10 wherein the biological signal is a thrombotic signal.

12. The flow system device of claim 10 wherein the fluid flow within the loop is controllable, such that flow dependent variations in the biological signal are generated.

13. The flow system device of claim 1 wherein the fluid flow within the loop is controllable such that the effects of background noise is minimized.

14. The flow system device of claim 1 wherein the loop has the geometric characteristics of a coronary arterial segment.

15. A method of creating, monitoring, and controlling specific, modifiable fluid flow patterns, said method comprises:
   providing a fluid flow system including at least one loop, a rotor stage for maintaining at least one rotor, the loop position on the rotor, a driving motor for rotating the rotor stage, a motion controller for controlling the speed and directional motion of the rotor, and an external measurement system to observe, record, and control the contained loop flow;
   filling the at least one loop with fluid which is to be tested;
   controlling the motor to obtain the desired motion of the fluid within the tube;
   measuring the desired effects of the fluid flow.

16. The method of claim 15 wherein the fluid is blood.

17. The method of claim 15 wherein a vascular prosthesis is maintained within the tube.

18. The method of claim 17 wherein the vascular prosthesis is a stent or graft.

19. The method of claim 17 wherein the biologic effect of the vascular prosthesis on the blood is measured.

20. The method of claim 19 wherein the loop has the geometric characteristics of a coronary arterial segment.

21. The method of claim 19 wherein the specific fluid flow pattern produced and observed is that of coronary flow.

22. The method of claim 19 wherein the biological effect is a thrombotic effect.

23. The method of claim 15 wherein the fluid flow within the loop is controlled, such that flow-dependent variations in the desired, measured effects are generated.

* * * * *

UNITED STATES PATENT AND TRADEMARK OFFICE
CERTIFICATE OF CORRECTION

PATENT NO. : 6,889,539 B2  
APPLICATION NO. : 10/629471  
DATED : May 10, 2005  
INVENTOR(S) : Elazer Edelman et al.

Page 1 of 1

It is certified that error appears in the above-identified patent and that said Letters Patent is hereby corrected as shown below:

Please insert the following in the specification of U.S. Patent no. 6,889,539 at column 1, line 3:

-- Sponsorship Information  
This invention was made with government support under Grant No. R01 GM049039 awarded by the National Institutes of Health. The government has certain rights in the invention. --

Signed and Sealed this  
Twentieth Day of December, 2011

David J. Kappos  
*Director of the United States Patent and Trademark Office*